United States Patent [19]

Hallenbach et al.

[11] Patent Number: 4,692,461

[45] Date of Patent: Sep. 8, 1987

[54] FUNGICIDAL THIENYLUREA DERIVATIVES

[75] Inventors: Werner Hallenbach, Langenfeld; Hans Lindel, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 933,492

[22] Filed: Nov. 21, 1986

[30] Foreign Application Priority Data

Nov. 26, 1985 [DE] Fed. Rep. of Germany ....... 3541628

[51] Int. Cl.[4] .................... A01N 43/02; C07D 333/56

[52] U.S. Cl. .................................... 514/443; 514/447; 549/57; 549/61; 549/69

[58] Field of Search ............................ 549/69, 57, 61; 514/443, 447

[56] References Cited

U.S. PATENT DOCUMENTS

| | | | |
|---|---|---|---|
| 3,705,910 | 12/1972 | Lundberg et al. | 549/57 |
| 3,823,161 | 7/1974 | Lesser | 260/332.2 C |
| 3,828,001 | 8/1974 | Broad et al. | 549/69 |
| 4,156,670 | 5/1979 | Asaro | 549/57 |

*Primary Examiner*—Alan Siegel

*Attorney, Agent, or Firm*—Sprung Horn Kramer & Woods

[57] ABSTRACT

Fungicidally active novel thienylurea derivatives of the formula

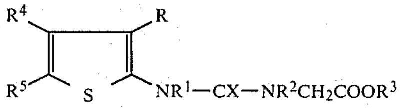

in which

X represents oxygen or sulphur,

R represents cyano, hydroxycarbonyl or alkoxycarbonyl, $R^1$ represents hydrogen or alkyl, $R^2$ represents hydrogen or alkyl, $R^3$ represents hydrogen, alkyl or optionally substituted aryl, $R^4$ represents hydrogen, alkyl or optionally substituted aryl, $R^5$ represents hydrogen, alkyl or optionally substituted aryl, or $R^4$ and $R^5$ together represent the radical $-(CH_2)_n-$, and n represents the numbers 3, 4, 5 or 6, or acid addition salts thereof.

17 Claims, No Drawings

FUNGICIDAL THIENYLUREA DERIVATIVES

The invention relates to new thienylurea derivatives, several processes for their preparation and their use in agents for combating pests, in particular as fungicides in plant protection.

It is already known that certain thienylureas, such as, for example, 1-(4,5-dimethyl-3-ethoxycarbonyl-2-thienyl)-3-methylurea, have a good fungicidal activity (compare, for example, U.S. Pat. No. 3,823,161). However, the action of these known compounds is not always completely satisfactory, especially in the case of low concentrations of active compound and when low amounts are applied.

New thienylurea derivatives of the formula (I)

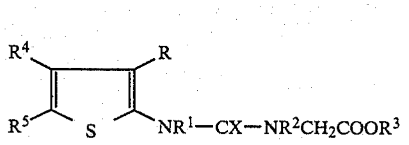

(I)

in which

X represents oxygen or sulphur,

R represents cyano, hydroxycarbonyl or alkoxycarbonyl, $R^1$ represents hydrogen or alkyl, $R^2$ represents hydrogen or alkyl, $R^3$ represents hydrogen, alkyl or optionally substituted aryl, $R^4$ represents hydrogen, alkyl or optionally substituted aryl and $R^5$ represents hydrogen, alkyl or optionally substituted aryl, or $R^4$ and $R^5$ together represent a radical $-(CH_2)_n-$, wherein n represents the numbers 3, 4, 5 or 6, and acid addition salts thereof, have now been found.

It has furthermore been found that the new thienylurea derivatives of the formula (I)

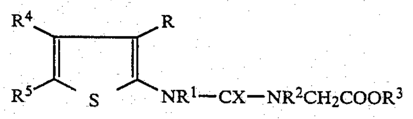

(I)

in which

X represents oxygen or sulphur,

R represents cyano, hydroxycarbonyl or alkoxycarbonyl, $R^1$ represents hydrogen or alkyl, $R^2$ represents hydrogen or alkyl, $R^3$ represents hydrogen, alkyl or optionally substituted aryl, $R^4$ represents hydrogen, alkyl or optionally substituted aryl and $R^5$ represents hydrogen, alkyl or optionally substituted aryl, or $R^4$ and $R^5$ together represent a radical $-(CH_2)_n-$, wherein n represents the numbers 3, 4, 5 or 6, and acid addition salts thereof, are obtained by a process in which (a) in the case where $R^2$ represents hydrogen, thienylamines of the formula (II)

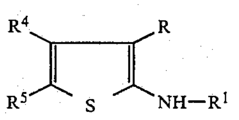

(II)

in which R, $R^1$, $R^4$ and $R^5$ have the abovementioned meanings, are reacted with iso(thio)cyanates of the formula (III)

$$XCNCH_2COOR_3 \qquad (III)$$

in which

X and $R^3$ have the abovementioned meanings, if appropriate in the presence of catalysts and if appropriate in the presence of diluents, or (b) in the case where $R^1$ represents hydrogen, thienyl iso(thio)cyanates of the formula (IV)

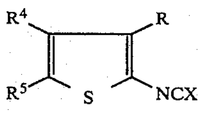

(IV)

in which X, R, $R^4$ and $R^5$ have the abovementioned meanings, are reacted with amino acids or acid addition salts thereof, of the formula (V)

$$HR^2N-CH_2COOR^3 \qquad (V)$$

in which $R^2$ and $R^3$ have the abovementioned meanings, if appropriate in the presence of catalysts and if appropriate in the presence of diluents, and, if appropriate, physiologically acceptable acids are added onto the compounds obtained.

The new thienylurea derivatives of the formula (I) are distinguished by a high activity as agents for combating pests, in particular by their outstanding selective fungicidal action.

The alky radicals $R^1$, $R^2$, $R^3$, $R^4$ and $R^5$ and the alkyl part of the alkoxycarbonyl radical R can be branched or straight-chain and preferably contain in each case 1 to 8, in particular 1 to 6 and particularly preferably 1 to 4, carbon atoms. Examples which may be mentioned are: methyl, ethyl, n-propyl, iso-propyl, n-butyl, iso-butyl, sec.-butyl, tert.-butyl, methoxycarbonyl, ethoxycarbonyl, n-propoxycarbonyl, iso-propoxycarbonyl, n-butoxycarbonyl, iso-butoxycarbonyl, sec.-butoxycarbonyl and tert.-butoxycarbonyl.

The optionally substituted aryl radicals $R^3$, $R^4$ and $R^5$ preferably contain 6 to 10 carbon atoms in the aryl part. Examples which may be mentioned are: optionally substituted naphthyl or phenyl, in particular optionally substituted phenyl.

The optionally substituted aryl radicals $R^3$, $R^4$ and $R^5$ can carry one or more, preferably 1 to 3 and in particular 1 or 2, identical or different substituents.

Examples of substituents which may be mentioned are: halogen, such as fluorine, chlorine and bromine; cyano; nitro; phenyl; phenoxy; phenylthio; alkyl with preferably 1 to 4, in particular 1 or 2, carbon atoms, such as methyl, ethyl, n- and i-propyl and n-, i-, sec.- and t-butyl; alkoxy with preferably 1 to 4, in particular 1 or 2, carbon atoms, such as methoxy, ethoxy, n- and i-propyloxy and n-, i-, sec.- and t-butyloxy; alkylthio with preferably 1 to 4, in particular 1 or 2, carbon atoms, such as methylthio, ethylthio, n- and i-propylthio and n-, i-, sec.- and t-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl; halogenoalkoxy with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethoxy; halogenoalkylthio with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethylthio; alkylcarbonyl with preferably 1 to 4, in particular 1 or 2, carbon atoms, such as methylcarbonyl and ethylcarbonyl; amino; alkylamino and dialkylamino with in each case preferably 1 to 4, in particular 1 or 2, carbon atoms, such as methylamino, ethylamino, n-propylamino, i-propylamino, n-butylamino, i-butylamino, dimethylamino, diethylamino, di-n-propylamino, di-i-propylamino, di-n-butylamino and di-i-butylamino; alkoxyalkyl with in each case preferably 1 to 4, in particular 1 or 2, carbon atoms in the alkyl part and alkoxy part, such as methoxymethyl, ethoxymethyl, methoxyethyl and ethoxyethyl; optionally halogen-substituted methylenedioxy or ethylenedioxy with, where appropriate, in each case 1 to 4 halogen atoms, halogen atoms being, preferably, fluorine, chlorine or bromine, in particular fluorine and/or chlorine.

The invention preferably relates to compounds of the formula (I) in which

X represents oxygen or sulphur,

R represents cyano, hydroxycarbonyl or alkoxycarbonyl with 1 to 6 carbon atoms in the alkyl part, $R^1$ represents hydrogen or alkyl with 1 to 4 carbon atoms, $R^2$ represents hydrogen or alkyl with 1 to 4 carbon atoms, $R^3$ represents hydrogen or alkyl with 1 to 6 carbon atoms, or represents phenyl which is optionally mono-, di- or trisubstituted by identical or different substituents from the group comprising fluorine; chlorine; bromine; $C_1$–$C_2$-alkyl; $C_1$–$C_2$-alkoxy; $C_1$–$C_2$-alkylthio; halogeno-$C_1$–$C_2$-alkyl, halogeno-$C_1$–$C_2$-alkoxy and halogeno-$C_1$–$C_2$-alkylthio with in each case 1 to 3 halogen atoms, such as fluorine, chlorine and/or bromine, in particular fluorine and/or chlorine; cyano; nitro; phenyl; phenoxy; phenylthio; $C_1$–$C_2$-alkoxy-carbonyl; amino; $C_1$–$C_2$-alkylamino, di-($C_1$–$C_2$)-alkylamino; $C_1$–$C_2$-alkoxy-$C_1$–$C_2$-alkyl and methylenedioxy and ethylenedioxy, optionally substituted by fluorine and/or chlorine, $R^4$ represents hydrogen or alkyl with 1 to 6 carbon atoms, or represents phenyl which is optionally mono-, di-, tri-, tetra- or pentasubstituted by identical or different substituents, preferred possible substituents on the phenyl being the substituents on the phenyl already mentioned in the case of $R^3$, and $R^5$ represents hydrogen, alkyl with 1 to 6 carbon atoms or phenyl which is optionally mono-, di- or trisubstituted by identical or different substituents, preferred possible substituents on the phenyl being the substituents on the phenyl already mentioned in the case of $R^3$, or $R^4$ and $R^5$ together represent a radical $-(CH_2)_n-$, wherein n represents the numbers 3, 4, 5 or 6.

Particularly preferred compounds of the formula (I) are those in which

X represents oxygen or sulphur,

R represents cyano, hydroxycarbonyl or $C_1$–$C_4$-alkoxycarbonyl, $R^1$ represents hydrogen or $C_1$–$C_2$-alkyl, $R^2$ represents hydrogen, or $C_1$–$C_2$-alkyl, $R^3$ represents hydrogen, $C_1$–$C_4$-alkyl or phenyl $R^4$ represents hydrogen, $C_1$–$C_4$-alkyl or phenyl and $R^5$ represents hydrogen, $C_1$–$C_4$-alkyl or phenyl, or $R^4$ and $R^5$ together represent a radical $-(CH_2)_n-$, wherein n represents the numbers 3, 4, 5 or 6.

Especially preferred compounds of the formula (I) are those in which

X represents oxygen,

R represents cyano, hydroxycarbonyl, methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl, $R^1$ represents hydrogen, $R^2$ represents hydrogen, $R^3$ represents hydrogen, methyl, ethyl, n-propyl, i-propyl, n-butyl, i-butyl, sec.-butyl or tert.-butyl, $R^4$ represents hydrogen, methyl, ethyl, n-propyl, i-propyl, n-butyl, i-butyl, sec.-butyl or tert.-butyl and $R^5$ represents hydrogen, phenyl, methyl, ethyl, n-propyl, i-propyl, n-butyl, i-butyl, sec.-butyl or tert.-butyl, or $R^4$ and $R^5$ together represent a radical $-(CH_2)_n-$, wherein n represents the numbers 3, 4, 5 or 6.

Compounds of the formula (I) which are furthermore especially preferred are those in which X represents sulphur, R represents hydroxycarbonyl, methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl, $R^1$ represents hydrogen, $R^2$ represents hydrogen, $R^3$ represents hydrogen, methyl, ethyl, n-propyl, i-propyl, n-butyl, i-butyl, sec.-butyl or tert.-butyl, $R^4$ represents hydrogen, methyl, ethyl, n-propyl, i-propyl, n-butyl, i-butyl, sec.-butyl or tert.-butyl and $R^5$ represents hydrogen, methyl, ethyl, n-propyl, i-propyl, n-butyl, i-butyl, sec.-butyl or tert.-butyl, or $R^4$ and $R^5$ together represent a radical $-(CH_2)_n-$, wherein n represents the numbers 3, 4, 5 or 6.

Addition products of acids and those thienylurea derivatives of the formula (I) in which the substituents R, $R^1$, $R^2R^3$, $R^4$ and $R^5$ have the meanings which have already been mentioned as preferred for these substituents are also preferred compounds according to the invention.

The acids which can be added on include, preferably, hydrogen halide acids, such as, for example, hydrochloric acid and hydrobromic acid, in particular hydrochloric acid, and furthermore phosphoric acid, sulphuric acid, nitric acid, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic acid, benzenesulphonic acid, trichloroacetic acid, phthalic acid, naphthalenesulphonic acid, nicotinic acid, citric acid and ascorbic acid.

If, for example, 3-methoxycarbonyl-4-methyl-2-methylamino-thiophene and methyl isocyanatoacetate are used as starting substances for process (a) according to the invention, the reaction can be outlined by the following equation:

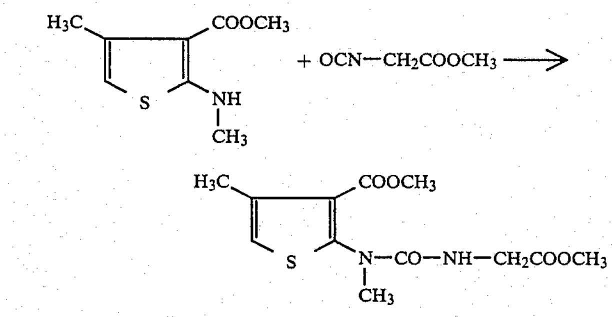

If, for example, 2-isocyanato-4-methyl-3-methoxycarbonyl-thiophene and glycine methyl ester are used as starting substances for process (b) according to the invention, the reaction can be outlined by the following equation:

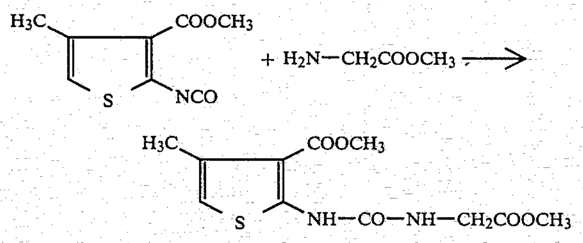

Formula (II) provides a definition of the thienylamines to be employed as starting substances for process (a) according to the invention. In this formula, R, $R^1$, $R^4$ and $R^5$ preferably represent those radicals which have been mentioned in the definition in the case of formula (I).

The compounds of the formula (II) are known or can be prepared analogously to known processes (compare, for example, K. Gewald Chem. Ber. 98 (1965), page 3571, Chem. Ber. 99 (1966), page 94. EP-OS (European Published Specification) No. 4,931 and G. Coppola et al J. Heterocycl. Chem. 1982, page 717).

The following compounds of the formula (II) may be mentioned specifically: 2-amino-3-cyano-4,5-trimethylene-thiophene, 2-amino-3-methoxycarbonyl-4,5-trimethylene-thiophene, 2-amino-3-ethoxycarbonyl-4,5-trimethylene-thiophene, 2-amino-3-t-butoxycarbonyl-4,5-trimethylene-thiophene, 2-amino-3-cyano-4,5-tetramethylene-thiophene, 2-amino-3-methoxycarbonyl-4,5-tetramethylene-thiophene, 2-amino-3-ethoxycarbonyl-4,5-tetramethylene-thiophene, 2-amino-3-t-butoxycarbonyl-4,5-tetramethylene-thiophene, 2-amino-3-cyano-4,5-pentamethylene-thiophene, 2-amino-3-methoxycarbonyl-4,5-pentamethylene-thiophene, 2-amino-3-ethoxycarbonyl-4,5-pentamethylene-thiophene, 2-amino-3-t-butoxycarbonyl-4,5-pentamethylene-thiophene, 2-amino-3-hydroxycarbonyl-thiophene, 2-amino-3-hydroxycarbonyl-4-methyl-thiophene, 2-amino-3-hydroxycarbonyl-5-methyl-thiophene, 2-amino-3-hydroxycarbonyl-4,5-dimethyl-thiophene, 2-amino-3-hydroxycarbonyl-4-ethyl-thiophene, 2-amino-3-hydroxycarbonyl-5-ethyl-thiophene, 2-amino-3-hydroxycarbonyl-4,5-diethyl-thiophene, 2-amino-3-hydroxycarbonyl-4-ethyl-5-methyl-thiophene, 2-amino-3-hydroxycarbonyl-4-methyl-5-ethyl-thiophene, 2-amino-3-hydroxycarbonyl-4-i-propyl-thiophene, 2-amino-3-hydroxycarbonyl-5-i-propylthiophene, 2-amino-3-hydroxycarbonyl-4-methyl-5-phenylthiophene, 2-amino-3-hydroxycarbonyl-4-ethyl-5-phenylthiophene, 2-amino-3-hydroxycarbonyl-5-phenyl-thiophene, 2-amino-3-methoxycarbonyl-thiophene, 2-amino-3-methoxycarbonyl-4-methyl-thiophene, 2-amino-3-methoxycarbonyl-5-methyl-thiophene, 2-amino-3-methoxycarbonyl-4,5-dimethylthiophene, 2-amino-3-methoxycarbonyl-4-ethyl-thiophene, 2-amino-3-methoxycarbonyl-5-ethyl-thiophene, 2-amino-3-methoxycarbonyl-4,5-diethyl-thiophene, 2-amino-3-methoxycarbonyl-4-ethyl-5-methyl-thiophene, 2-amino-3-methoxycarbonyl-4-methyl-5-ethyl-thiophene, 2-amino-3-methoxycarbonyl-4-i-propyl-thiophene, 2-amino-3-methoxycarbonyl-5-i-propyl-thiophene, 2-amino-3-ethoxycarbonyl-thiophene, 2-amino-3-ethoxycarbonyl-4-methyl-thiophene, 2-amino-3-ethoxycarbonyl-5-methyl-thiophene, 2-amino-3-ethoxycarbonyl-4,5-dimethyl-thiophene, 2-amino-3-ethoxycarbonyl-4-ethyl-thiophene, 2-amino-3-ethoxycarbonyl-5-ethyl-thiophene, 2-amino-3-ethoxycarbonyl-4,5-diethyl-thiophene, 2-amino-3-ethoxycarbonyl-4-ethyl-5-methyl-thiophene, 2-amino-3-ethoxycarbonyl-4-methyl-5-ethyl-thiophene, 2-amino-3-ethoxycarbonyl-4-i-propyl-thiophene, 2-amino-3-ethoxycarbonyl-5-i-propyl-thiophene, 2-amino-3-methoxycarbonyl-4-methyl-5-phenyl-thiophene, 2-amino-3-methoxycarbonyl-4-ethyl-5-phenyl-thiophene, 2-amino-3-methoxycarbonyl-5-phenyl-thiophene, 2-amino-3-ethoxycarbonyl-4-methyl-5-phenyl-thiophene, 2-amino-3-ethoxycarbonyl-4-ethyl-5-phenyl-thiophene, 2-amino-3-ethoxycarbonyl-5-phenyl-thiophene, 2-amino-3-cyano-thiophene, 2-amino-3-cyano-4-methyl-thiophene, 2-amino-3-cyano-5-methyl-thiophene, 2-amino-3-cyano-4,5-dimethyl-thiophene, 2-amino-3-cyano-4-ethyl-thiophene, 2-amino-3-cyano-5-ethyl-thiophene, 2-amino-3-cyano-4,5-diethyl-thiophene, 2-amino-3-cyano-4-ethyl-5-methyl-thiophene, 2-amino-3-cyano-4-methyl-5-ethyl-thiophene, 2-amino-3-cyano-4-i-propyl-thiophene, 2-amino-3-cyano-5-i-propyl-thiophene, 2-amino-3-cyano-4-methyl-5-phenyl-thiophene, 2-amino-3-cyano-4-ethyl-5-phenyl-thiophene and 2-amino-3-cyano-5-phenyl-thiophene and the corresponding 2-methylamino derivatives.

Formula (III) provides a definition of the iso(thio)cyanates likewise to be used as starting substances for process (a) according to the invention. In this formula, X and $R^3$ preferably represent those radicals which have been mentioned in the definition in the case of formula (I).

The compounds of the formula (III) are known (compare, for example, "Methoden der organischen Chemie" ("Methods of Organic Chemistry") (Houben-Weyl-Müller), Volume XV/2, page 183, Thieme Verlag - Stuttgart).

Examples which may be mentioned of the compounds of the formula (III) are: methyl isocyanato-acetate, ethyl isocyanato-acetate, n-propyl isocyanato-acetate, i-propyl isocyanato-acetate, n-butyl isocyanato-acetate, i-butyl isocyanato-acetate, sec.-butyl isocyanato-acetate, tert.-butyl isocyanato-acetate and phenyl isocyanato-acetate and the corresponding isothiocyanato derivatives.

The reaction (a) according to the invention between the thienylamines of the formula (II) and the iso(thio)-cyanates of the formula (III) is preferably carried out in the presence of a diluent. Suitable diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ester, tetrahydrofuran and dioxane, and moreover ketones, such as acetone, methyl ethyl ketone, methyl isopropyl ketone and methyl isobutyl ketone, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylene sulphone and hexamethylphosphoric acid triamide.

Catalysts may be added to accelerate process (a) according to the invention. Suitable catalysts are: for example tertiary amines, such as pyridine, 4-dimethylaminopyridine, triethylamine, triethylenediamine and trimethylene-tetrahydropyrimidine; and furthermore tin-II and tin-IV compounds, such as tin-II octoate or tin-IV chloride. The tertiary amines mentioned as reaction accelerators, for example pyridine, can also be used as solvents.

The reaction temperatures of process (a) according to the invention can be varied within a substantial temperature range. The reaction is in general carried out between 0° C. and 120° C., preferably between 20° and 70° C.

The reaction is usually carried out under normal pressure, but it may be advantageous, for example if low-boiling iso(thio)cyanates are used, for the reaction to be carried out in closed vessels under pressure.

In carrying out process (a) according to the invention, the starting substances of the formulae (II) and (III) are in general employed in stoichiometric ratios, but a slight excess of the isocyanate is favorable. The catalysts are preferably used in amounts of 0.01 to 0.1 mole per mole of the reaction components, but larger amounts, for example of the tertiary amines, can also be employed. The reaction products are isolated by a procedure in which products which precipitate directly from the corresponding solvents are filtered off, or the solvent is distilled off.

Formula (IV) provides a definition of the thienyl iso(thio)cyanates to be employed as starting substances for process (b) according to the invention. In this formula, X, R, $R^4$ and $R^5$ preferably represent those radicals which have been mentioned in the definition in the case of formula (I).

The compounds of the formula (IV) are known and/or can be prepared by known processes [compare, for example, DE-AS (German Published Specification) No. 2,040,579, DE-AS (German Published Specification) No. 2,122,636, EP-OS (European Published Specification) No. 4,931 and DE-AS (German Published Specification) No. 3,529,247].

Examples which may be mentioned of the compounds of the formula (IV) are: 2-isocyanato-3-cyano-4,5-trimethylene-thiophene, 2-isocyanato-3-methoxycarbonyl-4,5-trimethylene-thiophene, 2-isocyanato-3-ethoxycarbonyl-4,5-trimethylene-thiophene, 2-isocyanato-3-t-butoxycarbonyl-4,5-trimethylene-thiophene, 2-isocyanato-3-cyano-4,5-tetramethylene-thiophene, 2-isocyanato-3-methoxycarbonyl-4,5-tetramethylene-thiophene, 2-isocyanato-3-ethoxycarbonyl-4,5-tetramethylene-thiophene, 2-isocyanato-3-t-butoxycarbonyl-4,5-tetramethylene-thiophene, 2-isocyanato-3-cyano-4,5-pentamethylene-thiophene, 2-isocyanato-3-methoxycarbonyl-4,5-pentamethylene-thiophene, 2-isocyanato-3-ethoxycarbonyl-4,5-pentamethylene-thiophene, 2-isocyanato-3-t-butoxycarbonyl-4,5-pentamethylene-thiophene, 2-isocyanato-3-methoxycarbonyl-thiophene, 2-isocyanato-3-methoxycarbonyl-4-methyl-thiophene, 2-isocyanato-3-methoxycarbonyl-5-methyl-thiophene, 2-isocyanato-3-methoxycarbonyl-4,5-dimethyl-thiophene, 2-isocyanato-3-methoxycarbonyl-4-ethyl-thiophene, 2-isocyanato-3-methoxycarbonyl-5-ethylthiophene, 2-isocyanato-3-methoxycarbonyl-4,5-diethylthiophene, 2-isocyanato-3-methoxycarbonyl-4-ethyl-5-methyl-thiophene, 2-isocyanato-3-methoxycarbonyl-4-methyl-5-ethyl-thiophene, 2-isocyanato-3-methoxycarbonyl-4-i-propyl-thiophene, 2-isocyanato-3-methoxycarbonyl-5-i-propyl-thiophene, 2-isocyanato-3-ethoxycarbonyl-thiophene, 2-isocyanato-3-ethoxycarbonyl-4-methyl-thiophene, 2-isocyanato-3-ethoxycarbonyl-5-methyl-thiophene, 2-isocyanato-3-ethoxycarbonyl-4,5-dimethyl-thiophene, 2-isocyanato-3-ethoxycarbonyl-4-ethyl-thiophene, 2-isocyanato-3-ethoxycarbonyl-5-ethyl-thiophene, 2-isocyanato-3-ethoxycarbonyl-4,5-diethyl-thiophene, 2-isocyanato-3-ethoxycarbonyl-4-ethyl-5-methyl-thiophene, 2-isocyanato-3-ethoxycarbonyl-4-methyl-5-ethyl-thiophene, 2-isocyanato-3-ethoxycarbonyl-4-i-propyl-thiophene, 2-isocyanato-3-ethoxycarbonyl- 5-i-propyl-thiophene, 2-isocyanato-3-methoxycarbonyl-4-methyl-5-phenyl-thiophene, 2-isocyanato-3-methoxycarbonyl-4-ethyl-5-phenyl-thiophene, 2-isocyanato-3-methoxycarbonyl-5-pheny-thiophene, 2-isocyanato-3-ethoxycarbonyl-4-methyl-5-phenyl-thiophene, 2-isocyanato-3-ethoxycarbonyl-4-ethyl-5-phenyl-thiophene, 2-isocyanato-3-ethoxycarbonyl-5-phenyl-thiophene, 2-isocyanato-3-cyano-thiophene, 2-isocyanato-3-cyano-4-methyl-thiophene, 2-isocyanato-3-cyano-5-methyl-thiophene, 2-isocyanato-3-cyano-4,5-dimethyl-thiophene, 2-isocyanato-3-cyano-4-ethyl-thiophene, 2-isocyanato-3-cyano-5-ethyl-thiophene, 2-isocyanato-3-cyano-4,5-diethyl-thiophene, 2-isocyanato-3-cyano-4-ethyl-5-methyl-thiophene, 2-isocyanato-3-cyano-4-methyl-5-ethylthiophene, 2-isocyanato-3-cyano-4-i-propylthiophene, 2-isocyanato-3-cyano-5-i-propyl-thiophene, 2-isocyanato-3-cyano-4-methyl-5-phenyl-thiophene, 2-isocyanato-3-cyano-4-ethyl-5-phenyl-thiophene and 2-isocyanato-3-cyano-5-phenyl-thiophene and the corresponding 2-isothiocyanato derivatives.

Formula (V) provides a definition of the amino acids likewise to be used as starting substances for process (b). In this formula, $R^2$ and $R^3$ preferably represent those radicals which have been mentioned in the definition in the case of formula (I). The acid addition salts of the amino acids of the formula (V) can also be employed as starting substances for process (b). The acids which can be added on include, preferably, the acids which have already been mentioned for the acid addition salts of the compounds of the formula (I).

The compounds of the formula (V) are generally known compounds of organic chemistry.

Examples which may be mentioned of the compounds of the formula (V) and corresponding acid addition salts thereof are:

$$HR^2N—CH_2COOR_3 \quad (V)$$

TABLE 1

| $R^2$ | $R^3$ | $R^2$ | $R^3$ |
|---|---|---|---|
| H | $CH_3$ | $CH_3$ | $CH_3$ |
| H | $C_2H_5$ | $CH_3$ | $C_2H_5$ |
| H | $C_3H_7$-n | $CH_3$ | $C_3H_7$-n |
| H | $C_3H_7$-i | $CH_3$ | $C_3H_7$-i |
| H | $C_4H_9$-n | $CH_3$ | $C_4H_9$-n |
| H | $C_4H_9$-i | $CH_3$ | $C_4H_9$-i |
| H | $C_4H_9$-s | $CH_3$ | $C_4H_9$-s |
| H | $C_4H_9$-t | $CH_3$ | $C_4H_9$-t |
| H | H | $CH_3$ | H |
| H | 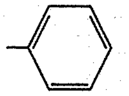 | $CH_3$ | 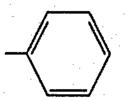 |

Process (b) according to the invention can be carried out with or without a diluent. Possible diluents are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylene sulphone and hexamethylphosphoric acid triamide.

Catalysts can be added to accelerate process (b) according to the invention. Suitable catalysts are: for example tertiary amines, such as pyridine, 4-dimethylaminopyridine, triethylamine, triethylenediamine and trimethylene-tetrahydropyrimidine; and furthermore tin-II and tin-IV compound, such as tin-II octoate or tin-IV chloride. The tertiary amines mentioned as reaction accelerators, for example pyridine, can also be used as solvents.

The reaction temperatures can be varied within a substantial temperature range. The reaction is in general carried out between 0° C. and 120° C., preferably between 20° C. and 70° C.

The reaction is usually carried out under normal pressure, but it may be advantageous, for example if low-boiling amines are used, for it to be carried out in closed vessels under pressure.

In carrying out process (b) according to the invention, the starting substances of the formulae (IV) and (V) are in general employed in stoichiometric ratios, but a slight excess of the amine is favorable. The catalysts are preferably used in amounts of 0.01 to 0.1 mole per mole of the reaction components, but larger amounts, for example of the tertiary amines, can also be employed.

The reaction products are isolated by a procedure in which products which precipitate out directly from the corresponding solvents are filtered off, or the solvent is distilled off.

The acid addition salts of the compounds of the formula (I) can be obtained in a simple manner by customary salt formation methods, for example by solving a compound of the formula (I) in a suitable inert solvent and adding the acid, for example hydrochloric acid, and they can be isolated in a known manner, for example by filtration, and if appropriate purified by washing with an inert organic solvent.

The active compounds according to the invention exhibit a powerful microbicidal action and can be employed in practice for combating undesired microorganisms. The active compounds are suitable for use as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The new active compounds display a particularly good activity against Botrytis fungi, for example against Botrytis cinerea, the causative organism of grey mould on French beans, lettuce, strawberries and vines.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorbenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

EXAMPLE A

Botrytis test (vines)/protective

Solvent: 4.7 parts by weight of acetone

Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, a clearly superior activity compared with the prior art is shown, for example, by the compounds according to preparation Examples (6) and (5).

Preparation Examples

EXAMPLE 1

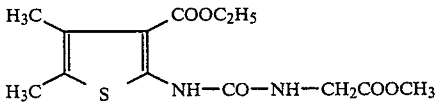

(Process (a))

4 g (0.35 mole) of methyl isocyanato-acetate are added to 5 g (0.22 mole) of 2-amino-4,5-dimethyl-3-ethoxycarbonyl-thiophene (in this context, compare Chem. Ber. 99, page 94–100 (1966)) in 30 ml of dry pyridine, and the mixture is warmed to 70° C. for 4 hours. After cooling, it is stirred into excess dilute hydrochloric acid and the precipitate is filtered off and recrystallized from ethanol.

2.6 g (37.3% of theory) of 1-(4,5-dimethyl-3-ethoxycarbonyl-2-thienyl)-3-methoxycarbonylmethyl-urea of melting point 151° C. are obtained.

EXAMPLE 2

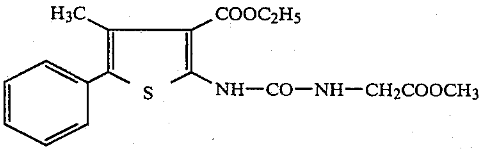

4.26 g (0.034 mole) of glycine methyl ester hydrochloride and 3.43 g (0.034 mole) of triethylamine are taken in 40 ml of dry chloroform, and 6.5 g (0.023 mole) of 3-ethoxycarbonyl-2-isocyanato-4-methyl-5-phenylthiophene, dissolved in 20 ml of dry chloroform, are added dropwise. The mixture is subsequently stirred for a further 30 minutes, and for working up it is poured onto 300 ml of water, the organic phase is separated off and the solvent is distilled off in vacuo. The residue is chromatographed over silica gel/methylene chloride.

5.3 g (62.3% of theory) of 1-(3-ethoxycarbonyl-4-methyl-5-phenyl-2-thienyl)-3-methoxycarbonylmethylurea are obtained.

IR (film) : 3400, 3000, 1740, 1660, 1550, 1520, 1220, 1050 and 1020 $cm^{-1}$.

The following compounds of the formula (I) can be prepared analogously to Example (1) and (2) or process (a) and (b);

TABLE 2

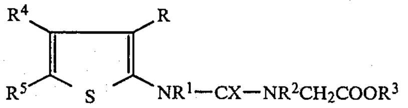 (I)

| Example No. | | $R^1$ | $R^2$ | $R^3$ | $R^4$ | $R^5$ | | Melting point [°C.] |
|---|---|---|---|---|---|---|---|---|
| 3 | $-COOC_2H_5$ | H | H | $-CH_3$ | H | H | O | 146 |
| 4 | $-COOC_2H_5$ | H | H | $-CH_3$ | $-C_2H_5$ | $-CH_3$ | O | 131 |
| 5 | $-COOH$ | H | H | $-CH_3$ | H | $-CH_3$ | O | 202 |
| 6 | $-COOC_2H_5$ | H | H | $-CH_3$ | $-(CH_2)_4-$ | | O | 166 |
| 7 | $-COOC_2H_5$ | H | H | $-CH_3$ | $-(CH_2)_5-$ | | O | 125 |
| 8 | $-COOC_4H_9-t$ | H | H | $-CH_3$ | $-(CH_2)_5-$ | | O | 109 |
| 9 | $-COOCH_3$ | H | H | $-CH_3$ | H | 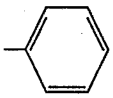 | O | |
| 10 | $-COOC_2H_5$ | H | H | $-CH_3$ | H | $-C_3H_7-i$ | O | 119 |
| 11 | $-COOCH_3$ | H | H | $-CH_3$ | $-CH_3$ | H | O | |
| 12 | $-COOC_2H_5$ | H | H | $-CH_3$ | H | $-CH_3$ | O | |
| 13 | $-COOC_2H_5$ | H | H | $-CH_3$ | $-CH_3$ | $-C_2H_5$ | O | |
| 14 | $-COOCH_3$ | H | H | $-CH_3$ | $-(CH_2)_3-$ | | O | 184 |
| 15 | $-COOC_2H_5$ | H | H | $-CH_3$ | $-(CH_2)_3-$ | | O | 173 |
| 16 | $-COOC_4H_9-t$ | H | H | $-CH_3$ | $-(CH_2)_3-$ | | O | 185 |
| 17 | $-CN$ | H | H | $-CH_3$ | $-(CH_2)_3-$ | | O | 168 |
| 18 | $-COOCH_3$ | H | H | $-CH_3$ | $-(CH_2)_4-$ | | O | 146 |
| 19 | $-COOC_4H_9-t$ | H | H | $-CH_3$ | $-(CH_2)_4-$ | | O | 01 |
| 20 | $-CN$ | H | H | $-CH_3$ | $-(CH_2)_4-$ | | O | 154 |
| 21 | $-COOCH_3$ | H | H | $-CH_3$ | $-(CH_2)_5-$ | | O | 123 |
| 22 | $-CN$ | H | H | $-CH_3$ | $-(CH_2)_4-$ | | O | 184 |
| 23 | $-COOC_2H_5$ | H | H | $-CH_3$ | H | H | S | |
| 24 | $-COOCH_3$ | H | H | $-CH_3$ | H | 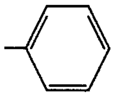 | S | |
| 25 | $-COOC_2H_5$ | H | H | $-CH_3$ | H | $-CH_3$ | S | |
| 26 | $-CN$ | H | H | $-CH_3$ | $-CH_3$ | H | O | 176 |
| 27 | $-CN$ | H | H | $-CH_3$ | H | H | O | 157 |
| 28 | $-CN$ | H | H | $-CH_3$ | H | $-CH_3$ | O | 159 |
| 29 | $-CN$ | H | H | $-C_2H_5$ | $-CH_3$ | $-CH_3$ | O | |

It is understood that the specification and examples are illustrative but not limitative of the present invention and that other embodiments within the spirit and scope of the invention will suggest themselves to those skilled in the art.

We claim:

1. A thienylurea derivative of the formula

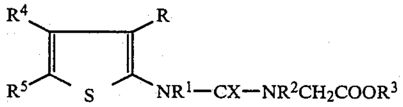

in which

X represents oxygen or sulphur,

R represents cyano, hydroxycarbonyl or alkoxycarbonyl, $R^1$ represents hydrogen or alkyl, $R^2$ represents hydrogen or alkyl, $R^3$ represents hydrogen, alkyl or optionally substituted aryl, $R^4$ represents hydrogen, alkyl or optionally substituted aryl, $R^5$ represents hydrogen, alkyl or optionally substituted aryl, or $R^4$ and $R^5$ together represent the radical $-(CH_2)_n-$, and n represents the numbers 3, 4, 5 or 6, or an acid addition salt thereof.

2. A thienylurea derivative or salt thereof according to claim 1, in which R represents cyano, hydroxycarbonyl or alkoxycarbonyl with 1 to 6 carbon atoms in the alkyl part, $R^1$ represents hydrogen or alkyl with 1 to 4 carbon atoms, $R^2$ represents hydrogen or alkyl with 1 to 4 carbon atoms, $R^3$ represents hydrogen or alkyl with 1 to 6 carbon atoms, or represents phenyl which is optionally mono-, di- or trisubstituted by identical or different substituents from the group consisting of fluorine; chlorine; bromine; $C_1$–$C_2$-alkyl; $C_1$–$C_2$-alkoxy; $C_1$–$C_2$-alkylthio; halogeno-$C_1$–$C_2$-alkyl, halogeno-$C_1$–$C_2$-alkoxy and halogeno-$C_1$–$C_2$-alkylthio with in each case 1 to 3 halogen atoms; cyano, nitro; phenyl; phenoxy; phenyltio; C.$C_2$-alkoxy-carbonyl; amino; $C_1$–$C_2$-alkylamino; di-($C_1$–$C_2$)-alkylamino; $C_1$–$C_2$-alkoxy-$C_1$–$C_2$-alkyl and methylenedioxy and ethylenedioxy, optionally substituted by fluorine and/or chlorine, $R^4$ represents hydrogen or alkyl with 1 to 6 carbon atoms, or represents phenyl which is optionally substituted by any of the phenyl substituents identified in the definition of $R^3$, and $R^5$ represents hydrogen, alkyl with 1 to 6 carbon atoms or phenyl which is optionally mono-, di- or trisubstituted by any of the phenyl substituents identified in the definition of $R^3$, or $R^4$ and $R^5$ together represent the radical $-(CH_2)_n-$.

3. A thienylurea derivative or salt thereof according to claim 1, in which R represents cyano, hydroxycarbonyl or $C_1$–$C_4$-alkoxycarbonyl, $R^1$ represents hydrogen or $C_1$–$C_2$-alkyl, $R^2$ represents hydrogen or $C_1$–$C_2$-alkyl, $R^3$ represents hydrogen, $C_1$–$C_4$-alkyl or phenyl, $R^4$ represents hydrogen, $C_1$–$C_4$-alkyl or phenyl and $R^5$ represents hydrogen, $C_1$–$C_4$-alkyl or phenyl, or $R^4$ and $R^5$ together represent the radical $-(CH_2)_n-$.

4. A thienylurea derivative or salt thereof according to claim 1, in which X represents oxygen, R represents cyano, hydroxycarbonyl, methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl, $R^1$ represents hydrogen, $R^2$ represents hydrogen, $R^3$ represents hydrogen, methyl, ethyl, n-propyl, i-propyl, n-butyl, i-butyl, sec.-butyl or tert.-butyl, $R^4$ represents hydrogen, methyl, ethyl, n-propyl, i-propyl, n-butyl, i-butyl, sec.-butyl or tert.-butyl and $R^4$ represents hydrogen, phenyl, methyl, ethyl, n-propyl, i-propyl, n-butyl, i-butyl, sec.-butyl or tert.-butyl, or $R^4$ and $R^5$ together represent the radical $-(CH_2)_n-$.

5. A thienylurea derivative or salt thereof according to claim 1, in which X represents sulphur, R represents hydroxycarbonyl, methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl, $R^1$ represents hydrogen, $R^2$ represents hydrogen, $R^3$ represents hydrogen, methyl, ethyl, n-propyl, i-propyl, n-butyl, i-butyl, sec.-butyl or tert.-butyl, $R^4$ represents hydrogen, methyl, ethyl, n-propyl, i-propyl, n-butyl, i-butyl, sec.-butyl or tert.-butyl and $R^5$ represents hydrogen, methyl, ethyl, n-propyl, i-propyl, n-butyl, i-butyl, sec.-butyl or tert.-butyl, or $R^4$ and $R^5$ together represent the radical $-(CH_2)_n-$.

6. A compound according to claim 1, wherein such compound is 1-(5-methyl-3-carboxy-2-thienyl)-3-methoxycarbonylmethyl-urea of the formula

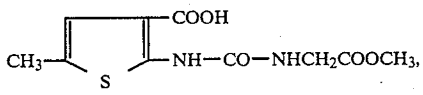

or an acid addition salt thereof.

7. A compound according to claim 1, wherein such compound is 1-(4,5-tetramethylene-3-ethoxycarbonyl-2-thienyl)-3-methoxycarbonylmethyl-urea of the formula

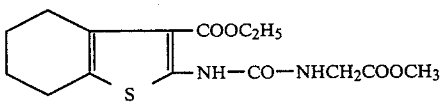

or an acid addition salt thereof.

8. A fungicidal composition comprising a fungicidally effective amount of a compound or salt according to claim 1 and a diluent.

9. A method of combating fungi which comprises applying to such fungi or to a fungus habitat a fungicidally effective amount of a compound or salt according to claim 1.

10. The method according to claim 9 wherein such compound is 1-(5-methyl-3-carboxy-2-thienyl)-3-methoxycarbonylmethyl-urea or 1-(4,5-tetramethylene-3-ethoxycarbonyl-2-thienyl)-3-methoxycarbonylmethyl-urea, or an acid addition salt thereof.

11. A method of combating fungi which comprises applying to such fungi or to a fungus habitat a fungicidally effective amount of a thienylurea derivative of the formula

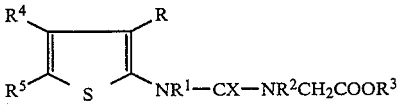

in which

X represents oxygen or sulphur,

R represents cyano, hydroxycarbonyl or alkoxycarbonyl, $R^1$ represents hydrogen or alkyl,
$R^2$ represents hydrogen or alkyl,
$R^3$ represents hydrogen, alkyl or optionally substituted aryl,
$R^4$ represents hydrogen, alkyl or optionally substituted aryl,
$R^5$ represents hydrogen, alkyl or optionally substituted aryl, or
$R^4$ and $R^5$ together represent the radical $-(CH_2)_n-$, and
n represents the numbers 3, 4, 5 or 6, or an acid addition salt thereof.

12. The method according to claim 11, in which
R represents cyano, hydroxycarbonyl or alkoxycarbonyl with 1 to 6 carbon atoms in the alkyl part,
$R^1$ represents hydrogen or alkyl with 1 to 4 carbon atoms,
$R^2$ represents hydrogen or alkyl with 1 to 4 carbon atoms,
$R^3$ represents hydrogen or alkyl with 1 to 6 carbon atoms, or represents phenyl which is optionally mono-, di- or trisubstituted by identical or different substituents from the group consisting of fluorine; chlorine; bromine; $C_1$–$C_2$-alkyl; $C_1$–$C_2$-alkoxy; $C_1$–$C_2$-alkylthio; halogeno-$C_1$–$C_2$-alkyl, halogeno-$C_1$–$C_2$-alkoxy and halogeno-$C_1$–$C_2$-alkylthio with in each case 1 to 3 halogen atoms; cyano; nitro; phenyl; phenoxy; phenylthio; $C_1$–$C_2$-alkoxy-carbonyl; amino; $C_1$–$C_2$-alkylamino; di-($C_1$–$C_2$)-alkylamino; $C_1$–$C_2$-alkoxy-$C_1$–$C_2$-alkyl and methylenedioxy and ethylenedioxy; optionally substituted by fluorine and/or chlorine,
$R^4$ represents hydrogen or alkyl with 1 to 6 carbon atoms, or represents phenyl which is optionally substituted by any of the phenyl substituents identified in the definition of $R^3$, and
$R^5$ represents hydrogen, alkyl with 1 to 6 carbon atoms or phenyl which is optionally mono-, di- or trisubstituted by any of the phenyl substituents identified in the difinition of $R^3$, or
$R^4$ and $R^5$ together represent the radical $-(CH_2)_n-$.

13. The method according to claim 11, in which
R represents cyano, hyhdroxycarbonyl or $C_1$–$C_4$-alkoxycarbonyl,
$R^1$ represents hydrogen or $C_1$–$C_2$-alkyl,
$R^2$ represents hydrogen or $C_1$–$C_2$-alkyl,
$R^3$ represents hydrogen, $C_1$–$C_4$-alkyl or phenyl,
$R^4$ represents hydrogen, $C_1$–$C_4$-alkyl or phenyl and
$R^5$ represents hydrogen, $C_1$–$C_4$-alkyl or phenyl, or
$R^4$ and $R^5$ together represent the radical $-(CH_2)_n-$.

14. The method according to claim 11, in which
X represents oxygen
R represents cyano, hydroxycarbonyl, methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl,
$R^1$ represents hydrogen,
$R^2$ reprensents hydrogen,
$R^3$ represents hydrogen, methyl, ethyl, n-propyl, i-propyl, n-butyl, i-butyl, sec.-butyl or tert.-butyl,
$R^4$ represents hydrogen, methyl, ethyl, n-propyl, i-propyl, n-butyl, i-butyl, sec.-butyl or tert.-butyl and
$R^4$ represents hydrogen, phenyl, methyl, ethyl, n-propyl, i-propyl, n-butyl, i-butyl, sec.-butyl or ter.-butyl, or
$R^4$ and $R^5$ together represent the radical $-(CH_2)_n-$.

15. The method according to claim 11, in which
X represents sulphur,
R represents hydroxycarbonyl, methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl,
$R^1$ represents hydrogen,
$R^2$ represents hydrogen,
$R^3$ represents hydrogen, methyl, ethyl, n-propyl, i-propyl, n-butyl, i-butyl, sec.-butyl or tert.-butyl,
$R^4$ represents hydrogen, methyl, ethyl, n-propyl, i-propyl, n-butyl, i-butyl, sec.-butyl or tert.-butyl and
$R^5$ represents hydrogen methyl, ethyl, n-propyl, i-propyl, n-butyl, i-butyl, sec.-butyl or tert.-butyl, or
$R^4$ and $R^5$ together represent the radical $-(CH_2)_n-$.

16. The method according to claim 11, wherein such theinylurea derivative is 1-(5-methyl-3-carboxy-2-thienyl)-3-methoxycarbonylmethyl-urea of the formula

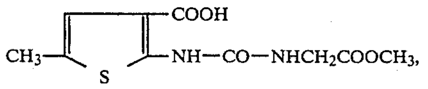

or an acid addition salt thereof.

17. The method according to claim 11, wherein such thienylurea derivative is 1-(4,5-tetramethylene-3-ethoxycarbonyl-2-thienyl)-3-methoxycarbonylmethyl-urea of the formula

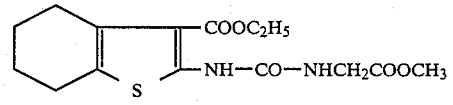

or an acid addition salt thereof.

* * * * *

UNITED STATES PATENT AND TRADEMARK OFFICE

CERTIFICATE OF CORRECTION

PATENT NO. : 4,692,461

DATED : September 8, 1987

INVENTOR(S) : Werner Hallenbach, et al.

It is certified that error appears in the above-identified patent and that said Letters Patent is hereby corrected as shown below:

On the title page "17 Claims" should read -- 7 Claims--.

| | |
|---|---|
| Col. 2, line 11 and Col. 9, line 5 | End of formula delete "$COOR_3$" and substitute --$COOR^3$-- |
| Col. 2, line 41 | Delete "alky" and substitute --alkyl-- |
| Col. 4, line 58 | After "$R^2$" insert --,-- |
| Col. 8, line 52 | Delete "propylthiophene" and substitute --propyl-thiophene-- |
| Col. 11, line 17 | Correct spelling of --chlorobenzenes-- |
| Col. 12, line 41 | Insert additional space after "C." |
| Col. 14, line 54 to Col. 16, line 54 | Cancel claims 1-10 in their entirety |
| Col. 17, line 30 | After "alkylamino" delete ";" and substitute --,-- |
| Col. 17, line 32 | After "ethylenedioxy" delete ";" and substitute --,-- |
| Col. 18, line 1 | After "oxygen" insert --,-- |
| Col. 18, line 8 | Correct spelling of --represents-- |
| Col. 18, line 14 | Delete "ter.-" and substitute --tert.- -- |
| Col. 18, line 34 | Correct spelling of --thienylurea-- |

Signed and Sealed this

Twenty-sixth Day of April, 1988

*Attest:*

DONALD J. QUIGG

*Attesting Officer* *Commissioner of Patents and Trademarks*